(12) United States Patent
Usui et al.

(10) Patent No.: US 8,083,888 B2
(45) Date of Patent: Dec. 27, 2011

(54) PLASMA PROCESSING APPARATUS

(75) Inventors: Tatehito Usui, Kasumigaura (JP); Tsuyoshi Yoshida, Hikari (JP); Tsuyoshi Matsumoto, Kudamatsu (JP); Satoru Muto, Kudamatsu (JP); Kenetsu Yokogawa, Tsurugashima (JP)

(73) Assignee: Hitachi High-Technologies Corporation, Tokyo (JP)

( * ) Notice: Subject to any disclaimer, the term of this patent is extended or adjusted under 35 U.S.C. 154(b) by 967 days.

(21) Appl. No.: 12/041,741

(22) Filed: Mar. 4, 2008

(65) Prior Publication Data

US 2009/0159211 A1 Jun. 25, 2009

(30) Foreign Application Priority Data

Dec. 19, 2007 (JP) ................................. 2007-327596

(51) Int. Cl.
*H01L 21/00* (2006.01)
*C23C 14/00* (2006.01)
*C23C 16/00* (2006.01)

(52) U.S. Cl. ......... 156/345.24; 156/345.25; 156/345.34; 118/715; 118/712

(58) Field of Classification Search ............. 156/345.24, 156/345.25, 345.34
See application file for complete search history.

(56) References Cited

U.S. PATENT DOCUMENTS

| 6,755,932 B2 * | 6/2004 | Masuda et al. ........... 156/345.24 |
| 6,758,941 B1 * | 7/2004 | Ookawa et al. .......... 156/345.47 |
| 2005/0092435 A1 * | 5/2005 | Hayashi et al. .......... 156/345.24 |
| 2005/0189069 A1 * | 9/2005 | Ludviksson et al. ..... 156/345.24 |
| 2006/0191484 A1 * | 8/2006 | Mitrovic et al. .............. 118/729 |
| 2007/0131354 A1 | 6/2007 | Yokogawa et al. |

FOREIGN PATENT DOCUMENTS

| JP | 2002-184766 | 6/2002 |
| JP | 3643540 | 2/2005 |
| JP | 2007-165512 | 6/2007 |

* cited by examiner

*Primary Examiner* — Ram N. Kackar
(74) *Attorney, Agent, or Firm* — Antonelli, Terry, Stout & Kraus, LLP.

(57) ABSTRACT

The invention provides a plasma processing apparatus for measuring the etching quantity of the material being processed and detecting the end point of etching using optical interference on the surface of a sample being processed, so as to simultaneously realize long life and ensure sufficient light to be received via a light transmitting unit, to enable long term stable operation and to improve the processing accuracy via accurate etching quantity detection. In a plasma processing apparatus for processing a sample being processed by generating plasma between a shower plate and a lower electrode, a detector for detecting light from a surface of the sample being processed via the shower plate includes a light transmitting unit composed of a light guide into which light is entered and a spectroscope for analyzing the light obtained by the light transmitting unit, wherein the end surface of the light transmitting unit through which light is entered is arranged at a distance of five times or greater of the mean free path of gas molecules within the vacuum reactor from the end surface of the shower plate facing the plasma.

2 Claims, 5 Drawing Sheets

PLASMA PROCESSING APPARATUS

The present application is underlayerd on and claims priority of Japanese patent application No. 2007-327596 filed on Dec. 19, 2007, the entire contents of which are hereby incorporated by reference.

BACKGROUND OF THE INVENTION

1. Field of the invention

The present invention relates to a semiconductor manufacturing apparatus for manufacturing semiconductor devices, and more specifically, relates to a dry etching technique for etching semiconductor materials such as silicon and silicon oxide films using plasma into profiles corresponding to a mask pattern formed of a resist material and the like.

2. Description of the related art

In the art of dry etching, material gas is introduced into a vacuum reactor having an evacuation means, and the material gas is turned into plasma via electromagnetic waves so as to expose the sample being processed to plasma to etch the areas of the surface of the sample being processed not covered by a mask, to thereby obtain the desired profile. High frequency voltage independent from plasma generation is applied to the sample being processed, and via the high frequency voltage, ions in the plasma are accelerated toward the surface of the sample being processed, by which the etching efficiency is improved and a perpendicular processing profile is obtained (refer for example to Japanese Patent Application Laid-Open Publication No. 2002-184766, hereinafter referred to as patent document 2).

In the art of dry etching, an endpoint detection for judging whether the etching of a predetermined quantity has been completed or not is normally performed by observing the plasma emission. Actually, the end point detection is performed by monitoring the quantity of emission of the reaction products of the material being etched in the plasma or the underlayer material exposed when etching is completed. However, from viewpoints of improvement of etching accuracy and reduction of costs by simplified processes, there are demands for not completing the etching when the underlayer material is exposed, but for stopping the etching process in midway of etching a single material or immediately prior to completing the etching.

According to such demands, the end point detection of etching cannot be performed by monitoring the emission from plasma as described above, but must be performed by monitoring either the etching quantity of the material being etched directly or the residual film thickness. A method for monitoring the etching quantity of the material being etched or the residual film thickness includes receiving light reflected on the surface of the sample being processed from plasma or from an independently-disposed light source, so as to analyze the interference pattern of the light accompanying the reduction of the material being etched on the surface of the sample being processed (refer for example to Japanese Patent No. 3643540, hereinafter referred to as patent document 1).

In etching apparatuses for etching insulating film materials such as silicon oxide films, a shower plate formed of a conductor such as silicon is disposed on an opposite side of the sample being processed, and high frequency power is applied to the whole body of the conductor including the shower plate to generate plasma. Thus, it is necessary to arrange a light transmitting unit to a conductor electrode portion opposed to the sample being processed, so as to monitor the etching quantity by performing analysis of the interference pattern of light accompanying the reduction of the material being etched. In general, a light transmitting unit has a structure to conduct light to the exterior of the vacuum reactor via a light guide rod formed for example of quartz or sapphire, and then to conduct the light via an optical fiber to a light interference pattern analysis unit composed for example of a spectroscope.

If the light guide formed for example of quartz or sapphire as the light transmitting unit is exposed directly to the shower plate surface formed for example of silicon, the end surface of the light guide rod is consumed by accelerated ions from the plasma or is subjected to deposition, making it impossible to receive light in an extremely short time. In order to overcome the problem, patent document 1 discloses a structure in which a plurality of penetrating holes 115B through which plasma cannot pass are formed to a portion of the silicon shower plate, and an optical transmitting rod 141 is arranged on the rear side of the shower plate.

According to the prior art example having the above-described structure, it becomes possible to significantly elongate the life for receiving light compared to when the light guide rod is directly exposed to plasma.

However, even by adopting the structure illustrated in patent document 1, it becomes difficult to receive light in approximately 100 to 200 hours of discharge time, which is an insufficient life according to the level of production performed in some semiconductor devices. Further, by taking measures such as reducing the diameter of the through holes formed to the shower plate and improving the aspect ratio, it becomes possible to extend the life of the light transmitting unit for some time, but the quantity of light passing therethrough is reduced, and the required accuracy cannot be ensured.

Further, in volume-production processes of semiconductors, it becomes necessary to replace the light guide rod when the light transmission rate of the rod is deteriorated. However, the prior art method has a drawback in that the replacement operation could not be performed easily.

SUMMARY OF THE INVENTION

The object of the present invention is to provide a plasma processing apparatus for determining the end point of etching by monitoring the etching quantity of the material being processed via light interference on the surface of the sample being processed, wherein a means is provided to realize both longer life of the light transmitting unit and ensured light receiving quantity, and to enable long-term stable operation and improved processing accuracy by accurately detecting the etching quantity.

The present invention provides a plasma processing apparatus comprising an upper electrode for supplying material gas into a vacuum reactor via a shower plate, a lower electrode opposed to the upper electrode on which is placed a sample being processed, and a detector for detecting light from a surface of the sample being processed via the shower plate, so as to process the sample by generating plasma between the shower plate and the lower electrode; wherein the detector comprises a light transmitting unit including a light guide into which the light is entered and a spectroscope for analyzing the light obtained through the light transmitting unit; and an end surface of the light transmitting unit through which the light is entered is positioned at a distance of five times or greater of a mean free path of a gas molecule within the vacuum reactor from an end surface of the shower plate facing the plasma.

Further, the present invention provides a light guide rod having a hollow structure in which a space is formed in the interior of the light guide rod. Further, the present invention provides a light guide rod having a convex shape so as to facilitate replacement of the light guide rod. Moreover, the rod may have a cylindrical member disposed within the hollow structure so as to prevent deposits from sticking to the light guide rod. Furthermore, the rod may have an insulating member disposed in the hollow structure so as to prevent abnormal plasma generation in the hollow structure.

The effects of the present invention are as follows. By arranging the end surface position of the light detecting unit at a distance of five times or greater of the mean free path of the gas within the vacuum reactor from the plasma boundary, it becomes possible to reduce the percentage of ions being accelerated from the plasma reaching the light transmitting unit directly in a collision less manner to 1/100 or smaller. Thus, it becomes possible to significantly suppress the consumption of the end surface of the light transmitting unit, and to elongate the life of the light transmitting unit to 1000 hours of discharge time or longer. Furthermore, by adopting a convex structure to the light guide rod, it becomes possible to reduce the operation time for exchanging rods to 1/10 or shorter.

DETAILED DESCRIPTION OF THE PREFERRED EMBODIMENTS

Now, the preferred embodiments of the present invention will be described with reference to the drawings.

Figure 1:
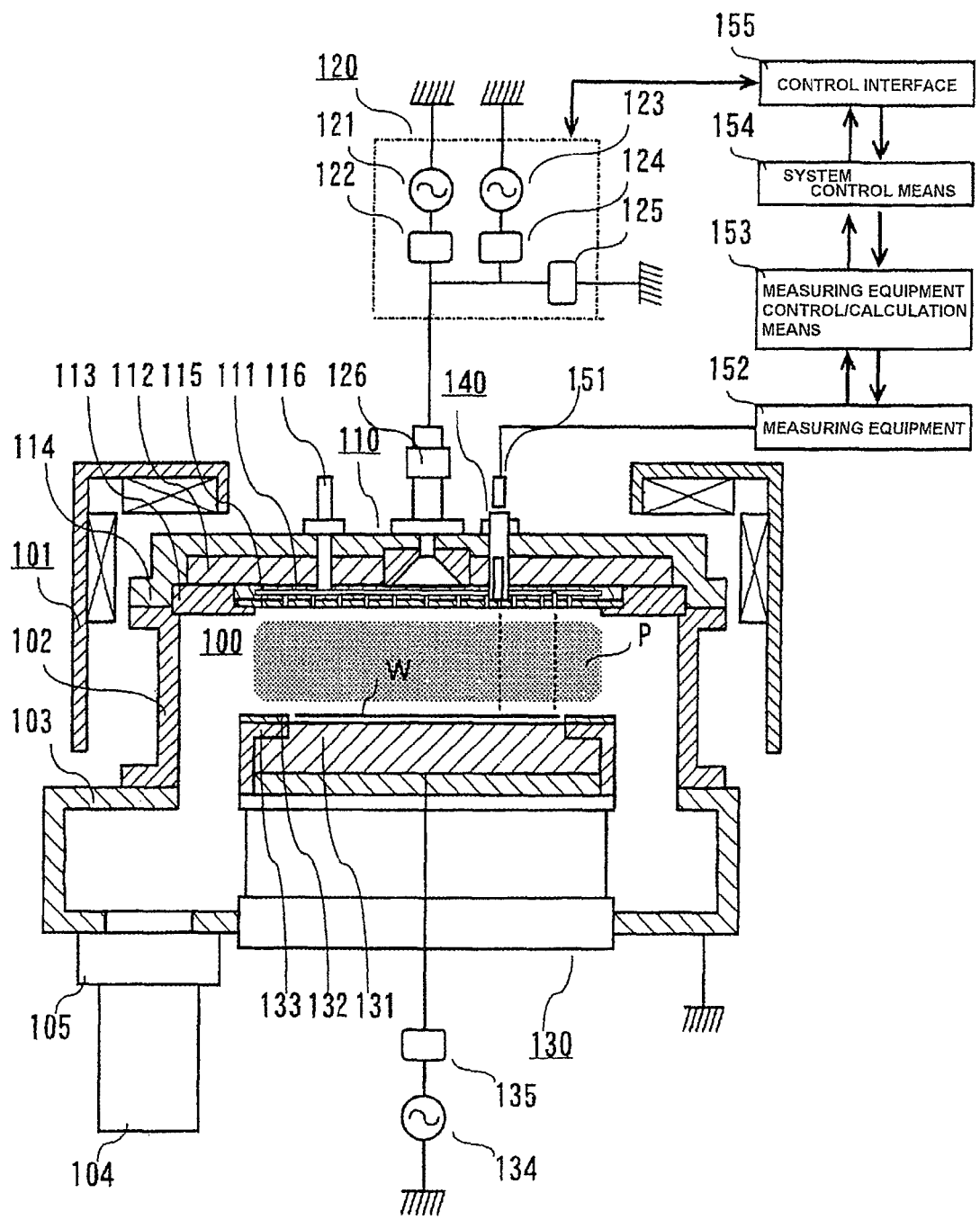
FIG. 1 is a view showing the basic structure of a plasma processing apparatus according to a first embodiment of the present invention.

FIG. 1 is a drawing showing the configuration of a plasma processing apparatus according to a first embodiment of the present invention, which illustrates an example in which the present invention is applied to a magnetic field UHF band electromagnetic radiation discharge-type plasma etching apparatus. FIG. 1 is a frame format showing the cross-section of the plasma etching apparatus according to the first embodiment.

In FIG. 1, a processing chamber 100 is disposed in the interior of a vacuum reactor capable of achieving a vacuum degree of approximately $10^{-6}$ Torr, and defines therein a space in which a substrate-shaped sample such as a semiconductor wafer is processed via plasma generated therein. An antenna 110 as plasma generating means for radiating electromagnetic waves is disposed on the upper portion in the interior of the vacuum reactor, and a lower electrode 130 on which the sample W such as a wafer is to be placed is disposed below the antenna 110.

The antenna 110 and the lower electrode 130 are disposed in parallel and opposed to one another. A magnetic field forming means 101 composed for example of an electromagnetic coil and a yoke is arranged in the circumference of the processing chamber 100, by which a magnetic field having a predetermined distribution and intensity is formed. By the interaction with the electromagnetic waves radiated from the antenna 110 and the magnetic field formed by the magnetic field forming means 101, plasma is generated from the processing gas supplied to the interior of the processing chamber, and the generated plasma P is used to process the wafer W placed on the lower electrode 130.

The processing chamber 100 is evacuated and pressure-controlled via an evacuation system 104 and a pressure control means 105 connected to the vacuum chamber 103, and the inner pressure of the chamber can be controlled to a predetermined value, which, for example, is in the range between 0.5 Pa and 4 Pa. The processing chamber 100 and the vacuum chamber 103 are set to earth potential. The temperature of the side wall 102 of the processing chamber 100 is controlled for example to 50° C. via a temperature control means not shown.

The antenna 110 for radiating electromagnetic waves is composed of a disk-shaped conductor 111, a dielectric body 112 and a dielectric ring 113, and supported on a housing 114 which constitutes a portion of the vacuum reactor. A structural body or disk-shaped plate 115 is disposed on one side of the disk-shaped conductor 111 which comes into contact with plasma, which is opposed to a wafer W or a circular sample-mounting plane of the upper surface of the lower electrode 130 described in detail later on which the wafer W is placed. The plate 115 is a circular plate-shaped conductive member, and the plate is fixed to position with respect to the disk-shaped conductor 111 on the outer circumference-side thereof. The diameter of the substantially circular portion of the plate 115 facing the plasma in the processing chamber 100 is either the same or greater than the diameter of the circular wafer W or the sample mounting plane.

The processing gas for subjecting the wafer W to processes such as etching and film deposition is fed from a gas supply means 116 with a predetermined flow rate and mixing ratio, which is homogenized in the interior of the disk-shaped conductor 111 and fed into the processing chamber through a plurality of holes formed to the plate 115. The temperature of the disk-shaped conductor 111 is controlled for example to 30° C. via a temperature control means not shown. An antenna power supply system 120 composed of an antenna power supply 121, an antenna bias power supply 123 and a matching circuit/filter system 122, 124 and 125 is connected via an introduction terminal 126 to the antenna 110. The antenna power supply 121 supplies a UHF-band frequency power preferably between 300 MHz and 900 MHz, so as to radiate UHF-band electromagnetic waves via the antenna 110.

The antenna bias power supply 123 applies a bias with a frequency of approximately 100 kHz or a few MHz to 10 MHz, for example, via the disk-shaped conductor 111 to the plate 115, and controls the reaction on the surface of the plate 115. Especially, in an oxide film etching process using CF-under layered gas, the material of the plate 115 is preferably formed of high-purity silicon or carbon, so as to enable control of the reaction of F radicals and CFx radicals on the surface of the plate 115 and to control the composition ratio of radicals. In the present embodiment, high-purity silicon is used for forming the plate 115.

The disk-shaped conductor 111 and the housing is formed of aluminum, and the dielectric body 112 and the dielectric ring 113 is formed of quartz. The distance between the lower surface of the plate 115 and the wafer W (hereinafter referred to as gap) is 30 mm or greater and 150 mm or smaller, preferably 50 mm or greater and 120 mm or smaller. In the present embodiment, the frequency of the antenna power supply 121 is set to 450 MHz, the frequency of the antenna bias power supply 122 is set to 13.56 MHz, and the gap is set to 70 mm.

A lower electrode 130 is disposed to face the antenna 110 at the lower portion of the processing chamber 100. On the upper surface or sample mounting surface of the lower electrode 130 is placed a wafer W, which is fixed thereto via an electrostatic chuck device 131. A sample stage ring 132 formed for example of high-purity silicon is disposed on an insulating body 133 at the outer circumference portion of the wafer W. A bias power supply 134 for supplying bias power in the range of preferably 400 kHz to 13.56 MHz is connected via a matching circuit/filter system 135 to the lower electrode 130, by which the bias power applied to the sample W is controlled.

In the present embodiment, the frequency of the bias power supply 134 is 800 kHz. Furthermore, an evacuation system 104 comprising a vacuum pump such as a turbo molecular pump is connected to the lower portion of the vacuum reactor disposed below the lower electrode 130, which is communicated with the interior of the processing chamber 100 via a port disposed at the bottom portion of the processing chamber 100. Through the operation of the evacuation system 104, the gas, plasma and particles generated by products formed by the processes in the processing chamber 100 are evacuated to the exterior of the processing chamber 100, and the interior of the processing chamber 100 is set to a pressure of a predetermined vacuum degree.

Next, a measurement port 140 disposed to measure the surface condition of the sample W, which is the substantial portion of the present embodiment, will be described. In the present embodiment, the measurement port 140 is attached by being inserted to the inner side of the antenna 110 facing the sample W, and through the multiple through holes formed to the plate 115, the status of the thin film or the like on the surface of the wafer W can be measured from the perpendicular upper direction. Of course, the mounting position of the measurement port is not restricted to the middle area as described above, but can be one or more than two locations arranged in different positions such as on the circumference area.

An optical transmission means 151 such as an optical fiber or lens is disposed on the opposite side from the wafer W via the plate 115 of the measurement port 140, and the optical information reflecting the surface condition of the wafer W, such as the direct light from the plasma P or the reflected light or interference light on the wafer W surface of the plasma P or the reference light such as the white light supplied into the processing chamber 100 are transmitted from the plate 115 via the optical transmission means 151 to a measuring equipment 152 composed for example of a camera, an interference film meter or an image processing apparatus for measurement. The measuring equipment 152 is controlled via a measuring equipment control/calculation means 153, and further connected to an upper system controlling means 154. The system controlling means 154 monitors and controls the status of the system via a control interface 155.

The plasma etching apparatus according to the present embodiment is composed as above, and the actual process for etching silicon oxide films or the like using the present plasma etching apparatus is as follows.

At first, a wafer W, which is the object being processed, is carried into the processing chamber 100 from a sample transfer mechanism not shown, which is then mounted and attracted to the lower electrode 130, and the height of the lower electrode is adjusted according to need to set the gap to a predetermined distance. Thereafter, the interior of the processing chamber 100 is vacuumed by the evacuation system 104, while gases required for the etching process of the wafer W, such as $C_4F_8$, Ar and $O_2$, are supplied from the gas supply means 116 with a predetermined flow rate and mixing ratio, such as 1000 sccm Ar, 43 sccm $CHF_3$ and 10 sccm $CF_4$, through the plate 115 of the antenna 110 to the processing chamber 100. At the same time, the interior of the processing chamber 100 is set to a predetermined processing pressure, such as 2 Pa.

On the other hand, a substantially horizontal magnetic field of substantially 160 Gauss corresponding to the intensity of an electron cyclotron resonance magnetic field with respect to the antenna power supply 121 with a frequency of 450 MHz is formed in the area below the plate 115. Then, electromagnetic waves in the UHF band is radiated via the antenna 110 from the antenna power supply 121, and plasma P is generated in the processing chamber 100 by the interaction with the magnetic field. Processing gas is dissociated and ion radicals are generated in the plasma P, and by further controlling the antenna bias power supply 123 and the bias power supply 134, the wafer W is subjected to etching and other processes.

The input power of the respective power supplies are, for example, 300 W for the antenna power supply 121, 200 W for the antenna bias power supply 123 and 160 W for the bias power supply 141. Then, at the end of the etching process, the supply of power and processing gas are stopped and the etching is ended.

Optical information reflecting the plasma emission and the surface condition of the wafer W during the process is transmitted through the measurement port 140 via the optical transmission means 151 to the measuring equipment 152 where measurement is performed, then underlayerd on the measured result, a measuring equipment control/calculation means 153 performs calculation, transmits the result to the upper system control means 154, and the plasma processing device system is controlled via a control interface 155.

Next, the detailed structure of a measurement port 140 will be described with reference to FIG. 2.

Figure 2:
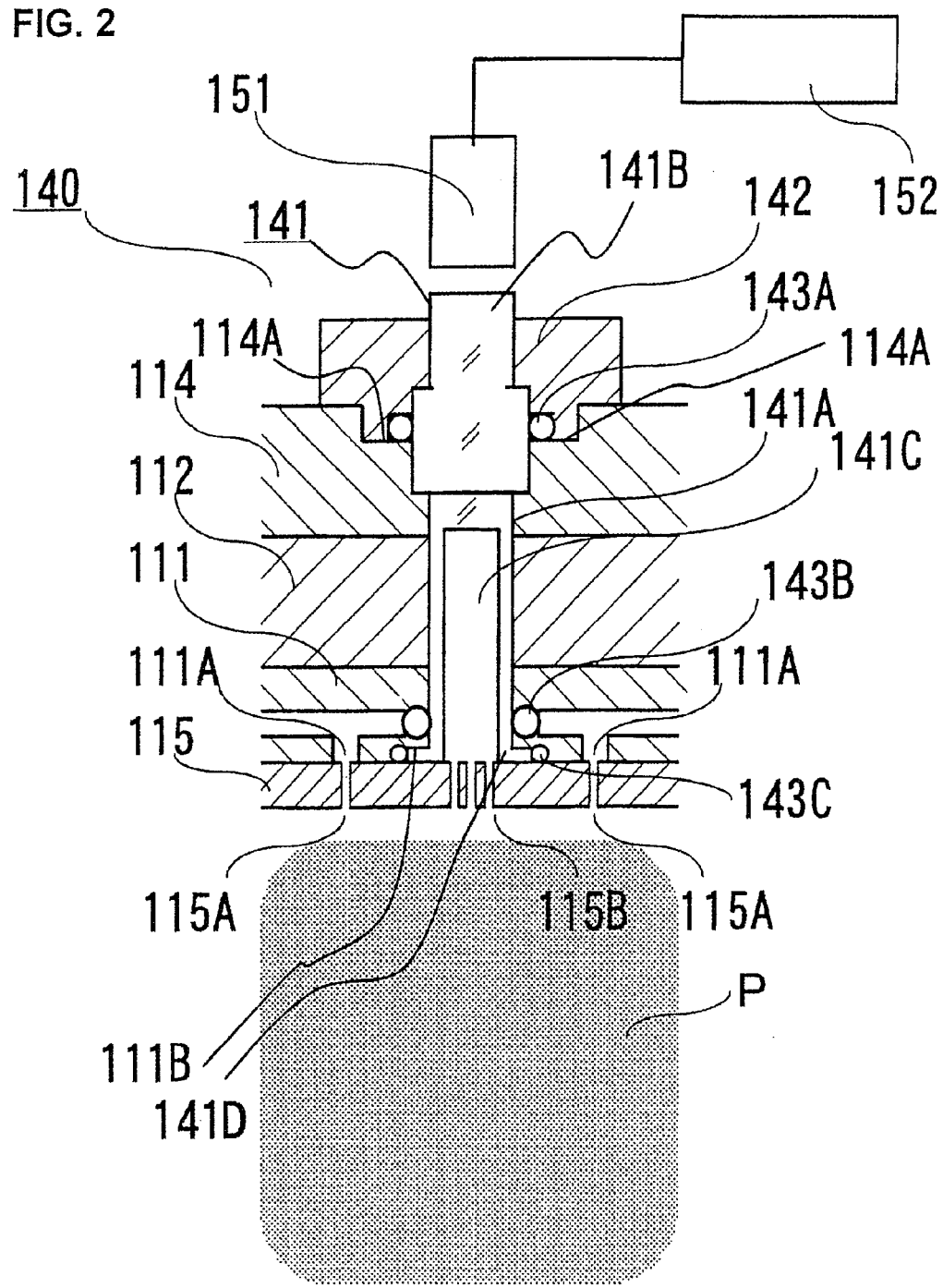
FIG. 2 is a detailed explanatory view showing the structure of a light detecting unit according to the first embodiment of the present invention.

FIG. 2 is a cross-sectional view showing in enlarged view a portion of the measurement port 140 attached to the antenna 110 in the embodiment of FIG. 1. As already described in FIG. 1, the disk-shaped conductor 111 and the dielectric body 112 forming the antenna 110 is supported by the housing 114, and a plate 115 is attached to the disk-shaped conductor 111. A number of gas through holes 115A are formed to the plate 115, and processing gas is supplied into the processing chamber 100 through gas through holes 111A formed at corresponding positions to the gas through holes 115A on a disk-shaped conductor 111 disposed above and adjacently covering the plate 115.

The gas through holes 115A formed to the plate 115 are through holes having a diameter in the range of approximately 0.1 mm to 5 mm, for example, preferably approximately 0.3 mm to 2 mm, and the gas through holes 111A formed on the disk-shaped conductor 111 are holes having an equal or greater diameter to the gas through holes 115A, the diameter of which is in the range of approximately 0.5 mm to 5 mm, for example, preferably approximately 2 mm. The thickness of the plate 115 is approximately 3 mm to 20 mm, and in the present embodiment, the thickness thereof is 10 mm.

A plurality of through holes 115B for receiving light which are cylindrical pores penetrated through the plate 115 are densely formed to the plate 115 at a position corresponding to the measurement port 140 disposed on the rear side of the plate. Above the opening on a rear side (side opposite from the plasma P) of the through holes 115B for receiving light on the plate 115 is disposed a light guide 141, which is placed at a position close to the rear side of the plate 115 either with a given gap therebetween, or with a minute gap therebetween so that the plate and the light guide are substantially considered to be in contact with each other, or mounted on the rear side.

The light guide 141 according to the present embodiment is composed of two parts that are separable into top and bottom portions, wherein the lower light guide 141A has its lower end arranged to face or substantially contact the plate 115, and the upper light guide 141B is mounted in a vacuum-sealed manner to the housing 114 via a retention means 142 and a vacuum sealing means 143A such as an O-ring. Then, an optical transmission means 151 such as an optical fiber or lens is disposed at the atmospheric end surface of the light guide 141. The direct light from the plasma P or the reflected light and interference light form the surface of the wafer W of the plasma P are transmitted through the through holes 115B for receiving light of the plate 115, transmitted through the light guide 141 to the optical transmission means 151, and further transmitted to the measuring equipment 152 for measurement.

The upper light guide 141B is positioned between the lower light guide 141A and the optical transmission means 151 to transmit the transmitted light or the optical information from the light guide 141A to the optical transmission means 151. The light guide 141B is a cylindrical member formed of quartz having a stepped shape in which the lower diameter is greater, wherein the lower large-diameter portion is inserted to the stepped upper surface of the cylindrical opening with multiple steps and having a diameter formed to correspond to the diameter of the lower large-diameter portion, by which the vertical position thereof is determined. The light guide is further covered by a retention means 142 fit thereto from above, and then screwed and attached to the housing 114 being grounded to ground potential. During this attaching operation, an o-ring disposed around the large-diameter portion is pressed against the light guide 141B by the engagement force by which the retention means 142 is screwed, by which the interior of the vacuum reactor is airtightly sealed from the exterior.

According to the present embodiment, the light guides 141A and 141B are cylindrical rods formed of quartz with steps and having multiple varying diameters. The diameter at the upper portion of the light guide 141A is preferably between approximately 5 mm and 30 mm, and in the present embodiment, the diameter is 8 mm. The light guide 141A has a cylindrical hole, in other words, a hollow structure or hollow space 141C, that is recessed to a predetermined depth in the axial direction of the cylinder from the end surface that faces or opposes to the through holes 115B for receiving light of the plate 115 when the measurement port 140 is attached thereto.

In the present embodiment, the inner diameter of the cylindrical hollow space 141C is 6 mm, and the depth thereof is 15 mm. Similar to the gas through holes 115A, the through holes 115B for receiving light has a diameter of approximately 0.1 mm to 5 mm, preferably approximately 0.3 mm to 2 mm, and in the present embodiment, the diameter of the through holes 115B is 0.5 mm. Further, a multiple number of through holes 115B for receiving light should be provided so as to improve the measurement sensitivity. Seven through holes are provided in the present embodiment.

The area in which the through holes 115B for receiving light are formed is within the opening on the lower end of the hollow space 141C when the light guide 141A is attached to the antenna 110, and the outer edge of the hollow space 141C of the light guide 141A is arranged to surround the multiple through holes 115B for receiving light. The hollow space 141C can be formed by cutting and hollowing the interior of the cylindrically-shaped quartz material along the axis of the cylinder from one end to the other end, as according to the present invention, or by attaching a cylindrical member to a pipe-like member.

Further, the light guide 141A is structured so that the outer diameter of the portion positioned toward the plate 115 is formed greater than the rod diameter (projected or convex structure) so as to facilitate the replacing operation of the light guide 141A. According especially to the present embodiment, the lower end portion facing the plate 115 of the light guide is extended outward in a flange to form a flange portion 141D having a diameter of 10 mm and a length of 1.5 mm. In order to prevent supplied gas from directly flowing into the hollow space 141C of the light guide 141, vacuum seal means 143B and 143C, such as o-rings, are disposed in the circumference of the light guide 141.

In other words, an o-ring, which is the vacuum seal means 143B, is disposed on the outer circumference of the side wall of the upper cylindrical portion or small-diameter portion, sealing the space between the side wall and the gas reservoir space at the inner side of the cylindrical conductor 111. Further, an o-ring, which is the vacuum seal means 143C, is fit to the outer circumference of the flanged portion 141D and the inner wall of the cylindrical recess disposed on the lower surface facing the plasma of the disk-shaped conductor 111, airtightly sealing the space between the disk-shaped conductor 111 and the gas through holes 111A and 115A. The two vacuum seal means 143B and 143C prevent the particles of gas supplied to the processing chamber 100 or particles from the gas and plasma in the processing chamber from entering the upper portion of the light guide 141A and contaminating the interior of the antenna 110 or the surface of the light guides 141A and 141B.

Further, a cylindrical recess is arranged around the through hole at the lower surface of the disk-shaped conductor 111 into which the light guide 141A is inserted, and when the light guide 141A is inserted to the through hole of the disk-shaped conductor 111, the flange portion 141D is stored in the interior of the recess and the vertical position of the light guide is determined by the upper surface of the stepped portion 111B of the recess. Moreover, an o-ring which is the vacuum seal means 143C is fit to the recess of the disk-shaped conductor 111 at the outer circumference portion of the flange portion 141D.

As described, when the plate 115 is supported and fixed at the outer circumference to the disk-shaped conductor 111, the vacuum seal means 143C is sandwiched and supported by the plate 115, the upper or side surface of the stepped portion 111D of the recess and the flange portion 141D and pressed thereto, so as to seal the space between the interior of the light guide 141C, the through holes 115B for receiving light and the gas through holes 111A and 115A, and the vertical and horizontal position of the light guide 141A is determined and fixed thereby.

Further, the material of the light guide 141A and 141B is selected from a group consisting of quartz, sapphire, YAG (yttrium-aluminum-garnet) and yttria crystal ($Y_2O_3$), preferably sapphire, YAG and $Y_2O_3$. Sapphire, YAG and yttria crystal are expensive but generally not easily sputtered compared to quartz, and therefore, a longer life is expected by using these materials instead of quartz.

According to the present embodiment, light guide rods 141A and 141B are disposed to receive the reflected light from the wafer W via through holes 115B for receiving light formed to the shower plate 115 and the hollow space 141C.

Further, the length of the hollow space 141C is set so that the distance from the plasma P side of the shower plate 115 to the upper end of the hollow space 141C of the light guide rod 141A, that is, to the opposite end farthest from the plasma P via the plate, is five times or greater of the mean free path of the gas molecules under a gas pressure condition in the plasma generating atmosphere within the vacuum reactor 144.

The through holes 115B for receiving light formed to the shower plate 115 has a function to block plasma P. In the present embodiment, the diameter of each of the through holes 115B for receiving light is 0.5 mm. This arrangement enables to prevent gas and charged particles in the plasma P from entering the hollow space 141C. According to the present embodiment, the end surface of the light guide rod 141 disposed at the depth of the hollow space 141C formed on the rear surface of the plate 115 from the processing chamber is arranged at a position sufficiently spaced apart from the plasma P. In other words, according to the present embodiment, the end surface of the light guide rod is disposed via the hollow space 141C with a length of 15 mm.

Accordingly, the distance from the plasma P to the end surface of the light guide rod is 25 mm, which is seven to eight times the mean free path of the gas molecules in a 2 Pa atmosphere. Therefore, the end surface of the rod for introducing light is exposed to very little ion radiation, by which the chances of the end surface of the rod being consumed are reduced, so that the rod can have a longer life. As described, by forming a hollow space 141C in the light guide rod 141, the life of the light guide rod 141 can be extended, and since the light guide rod 141 is projected at the outer circumference portion, the operator can easily grip and handle the light guide 141, by which the time required for the replacing operation of components can be shortened.

Further, since the inner diameter of the hollow space 141C is approximately 5 mm or greater, the light guide rod 141A can be cleaned easily for recycle, so that the cost of replacing the components can be reduced. According further to the present embodiment, the light guide 141 is divided into the lower light guide 141A and the upper light guide 141B. The light guides 141A and 141B are respectively inserted to the through holes of the disk-shaped conductor 111 and the housing 114 and supported within the antenna 110, and the light guides are respectively determined of their positions on the surface of the stepped portion 111B of the recessed portion and the stepped portion 114A of the housing 114.

By screw-engaging the retention means 142, the upper light guide 141B is pressed against the upper surface of the stepped portion 114A by the vacuum seal means 143A and the retention means 142, by which the vertical position thereof is determined and retained. Further, the lower light guide 141A is designed so that when the housing 114 is rotated upward to release the processing chamber 100 by which the plate 115 is separated from the disk-shaped conductor 111, the lower light guide 141A can be attached and detached substantially perpendicularly with respect to the antenna 110 or the disk-shaped conductor 111. When the lower light guide 141A is inserted to the through hole of the disk-shaped conductor 111 and the flange portion 141D is fit to the stepped portion 111B of the recess, and when the vacuum seal means 143C on the outer circumference is mounted to the recessed portion and the plate 115 is attached, the upper surface of the flange portion 141D opposing to the disk-shaped conductor 111 is positioned with respect to the surface of the stepped portion 111B.

For example, the o-ring or vacuum seal means 143C is positioned between the plate 115 and the flange portion 141D to apply a force to press the flange portion 141D toward the stepped portion 111B of the disk-shaped conductor 111 (toward the upper direction when the housing 114 is closed), so as to hold the light guide 141A between the disk-shaped conductor 111 (or the stepped portion 111B thereof) and the vacuum seal means 143C (or plate 115) and determine the vertical position thereof.

In this case, a minute gap is formed between the end surface of the flange portion 141D facing the plate and the rear surface of the plate 115, and the shapes of the stepped portion 111B and the flange portion 141D are designed so that the size of the gap does not cause abnormal electrical discharge by the electric field formed by the supplied high frequency. It is also possible to dispose the flange portion 141D and the rear surface of the plate 115 to either contact one another or be closely arranged so that they are substantially considered to be in contact with one another, and to form a minute gap between the flange portion 141D and the stepped portion 111B of the disk-shaped conductor 111 small enough not to cause abnormal electrical discharge.

Moreover, the cylindrical light guides 141A and 141B having their vertical positions determined respectively are also positioned so that the space between the upper end surface and the lower end surface of the light guides 141A and 141B is small enough so as not to cause abnormal electrical discharge by the above-mentioned electric field formed via high frequency. According to such arrangement of positioning, it becomes possible to prevent the occurrence of abnormal electrical discharge in the gap formed between and around the light guides 141A and 141B, and also suppress the light in the processing chamber 100 passing through the through holes 115B for receiving light and the hollow space 141C and through the light guide 141A to the light guide 141B from being attenuated by abnormal reflections or inflections, by which the reliability of the light guide 141 is improved, along with the suppression of optical attenuation caused by contamination and damage of the interior of the hollow space 141C by particles from the plasma P.

Figure 3:
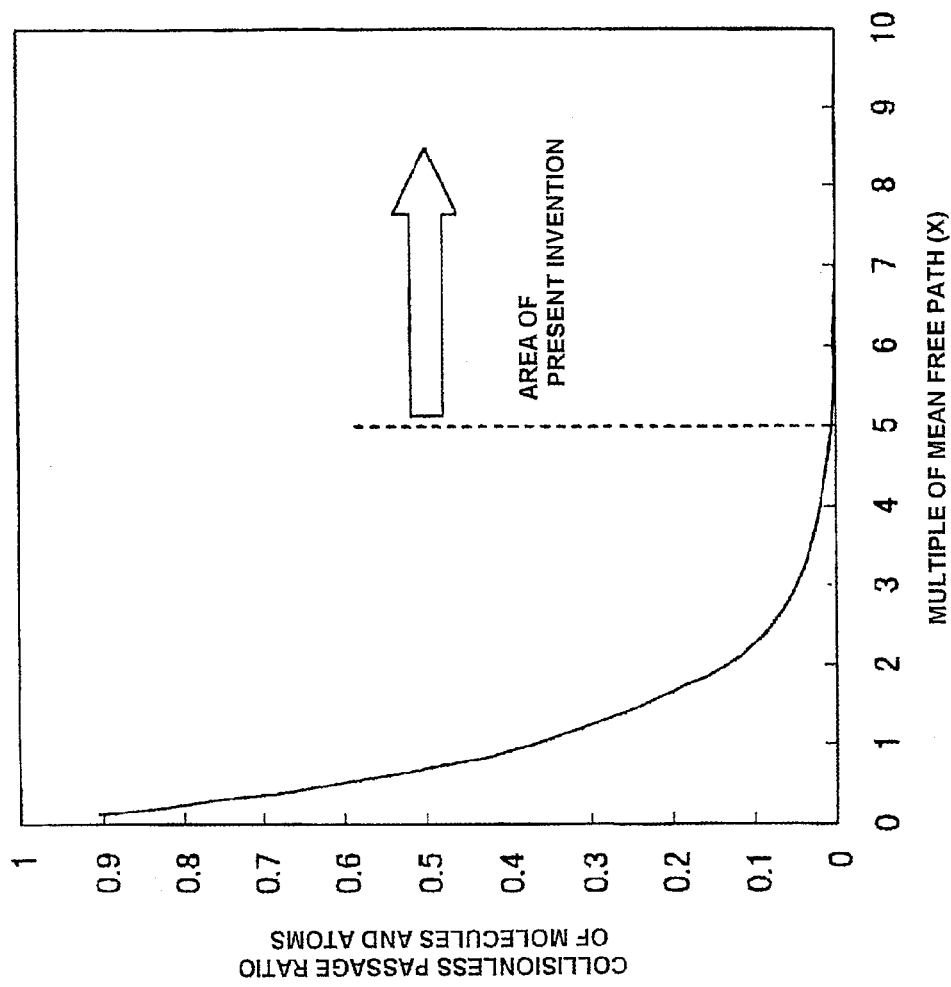
FIG. 3 is a view showing the multiples of mean free path and the ratio of molecules and atoms passing the distance in a collisionless manner.

With reference to FIG. 3, a collisionless passage ratio of molecules and atoms with respect to the multiple of mean free path will be described. The collisionless passage ratio of molecules and atoms is reduced exponentially with respect to the multiple of the mean free path. From FIG. 3, when molecules and atoms pass approximately five times the distance of the mean free path, the percentage in which the molecules and atoms can pass the distance in a collisionless manner is 1% or less, meaning that most molecules and atoms experience collision within the gas phase and lose their initial kinetic energy. When the distance is approximately seven to eight times the mean free path, the percentage in which the molecules and atoms pass in a collisionless manner is 0.1% or smaller.

Thus, according to the arrangement illustrated in the present embodiment, the percentage of the ions accelerated in the plasma P and reaching the end surface of the light guide rod in a collisionless manner is 0.1% or smaller. According to the prior art method in which the end surface of the light guide rod is positioned immediately behind the shower plate 115, the distance is two to three times the mean free path, meaning that according to FIG. 3, the percentage of ions reaching the end surface of the light guide rod in a collisionless manner is approximately 5 to 15%. Therefore, according to the arrangement of the present embodiment, the percentage of ions reaching the end surface of the light guide rod in a collisionless manner is $1/50$ to $1/150$ the percentage thereof according to the prior art arrangement, so that according to the present invention, the life of the end surface of the light guide rod cab be extended significantly. As a result of actual evaluation, the arrangement of the present invention enables to ensure sufficient lighting quantity after a discharge time of 1000 hours, which is five times or greater than the prior art method.

Modified Example 1

Figure 4:
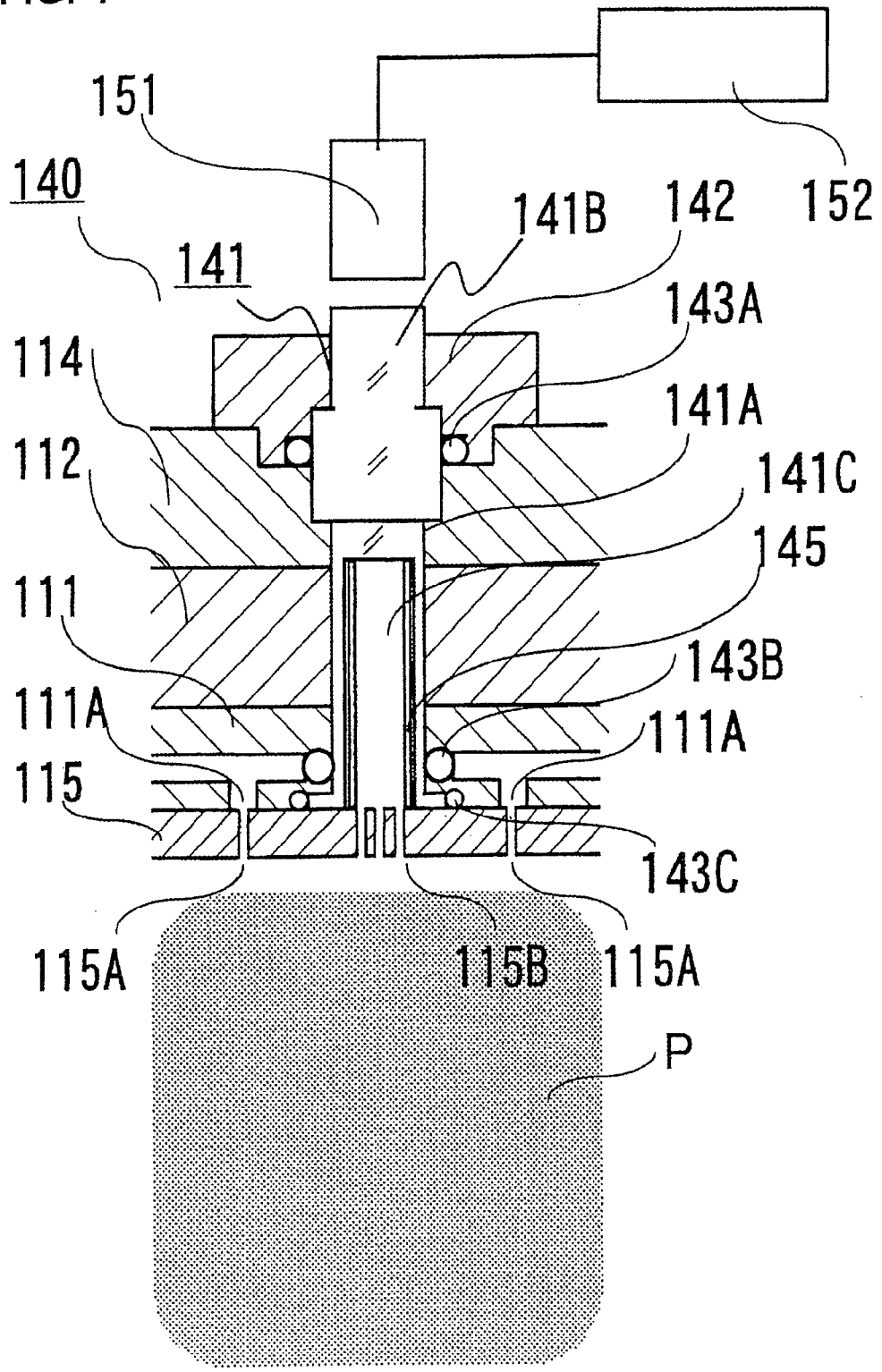
FIG. 4 is a detailed explanatory view of the structure of a light detecting unit according to a first modified example of the present invention.

A modified example of the present invention will now be described with reference to FIG. 4. Similar to FIG. 2 of the first embodiment, FIG. 4 is a view showing the detailed structure of a measurement port 140. FIG. 4 characterizes in that a pipe member 145 is disposed in the interior of the hollow space 141C of the light guide rod 141. The pipe member 145 is positioned inside the hollow space 141C of the light guide rod 141.

If the pipe member 145 is not arranged, the ions, molecules and atoms scattered in the hollow space 141C stick to the side wall of the hollow space 141C, by which deposits are formed on the side walls. The deposits stuck to the side wall will come off within a time shorter than the life of the end surface of the light guide rod 141, causing contaminants that may interrupt the production processes of etching, by which the light guide rod 141 may have to be replaced. However, by placing a pipe member 145 in the hollow space 141C of the light guide rod 141, it becomes possible to attach the deposits such as scattered ions, molecules and atoms to the inner wall of the pipe member 145, and to enable the replacement operation to be performed in a short time since only the pipe member 145 must be replaced.

Further, by creating a multilayered wall surface within the hollow space 141C by placing the pipe member 145, and by further forming patterns on the inner wall thereof so as to increase the surface area of the inner wall, it becomes possible to reduce the thickness of the deposits on the inner wall of the pipe member 145, so as to extend the replacement life of the pipe member 145. For example, if grooves with a width of 0.1 mm with an inner diameter of 4.75 mm are patterned on the pipe member 145 having an inner diameter of 4.5 mm and a length of 14.5 mm, the surface area of the inner wall will be increased from 230.5 mm$^2$ to 770 mm$^2$, so that the surface area is increased by approximately 3.3 times, and if grooves with a width of 0.01 mm are patterned on the pipe member, the surface area becomes 5508 mm$^2$, by which the surface area is increased by approximately seven times, and the life thereof is extended.

As described, the arrangement of the pipe member 145 enables to extend the life of the light guide rod 141 and to reduce the operation time required for replacing the components when particles are generated. Further, by extending the life of the light guide rod 141, it becomes possible to reduce the costs of the replaced components. Further, it is possible to position at least one of the multiple through holes 115B for receiving light to the area between the outer circumference of the inner wall of the hollow space 141C on the end adjacent to the plate and the outer circumference of the end portion of the pipe member 145, so as to allow particles from the plasma P to enter the space formed therebetween.

Modified Example 2

Figure 5:
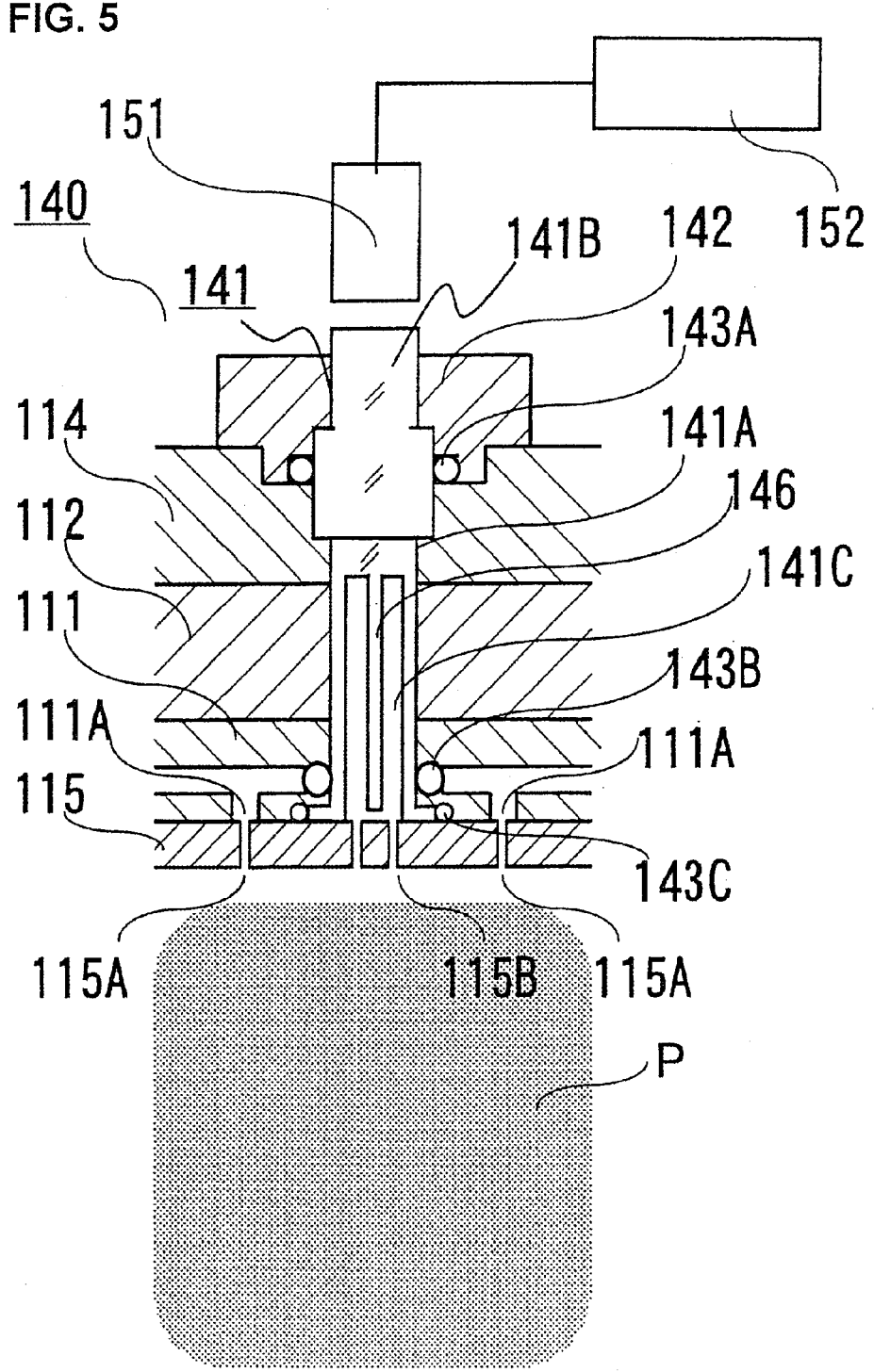
FIG. 5 is a detailed explanatory view of the structure of a light detecting unit according to a second modified example of the present invention.

A second modified example of the present invention will be described with reference to FIG. 5. FIG. 5 is a view illustrating the detailed structure of a measurement port 140, similar to FIG. 2 of embodiment 1. FIG. 5 characterizes in that an insulating member component 146 formed of a cylindrical quartz extended from the bottom portion of the hollow space 141C toward the rear surface of the plate 115 is arranged in the interior of and in correspondence with the center axis of the hollow space 141C which is a cylindrically recessed portion of the light guide rod 141.

The cylindrical insulating member component 146 can be formed integrally when forming the main body of the light guide 141A, or by inserting a separately formed cylindrical component to the hollow space 141C of the light guide 141A and assembling the components together. Further, it is preferable that a minute gap is formed between the leading end disposed toward the plate 115 of the insulating member component 146 and the rear surface of the plate 115 opposed thereto, and that no through holes 115B for receiving light are positioned in this area on the rear surface of the plate 115.

If there is no insulating member component 146, according to some etching conditions (such as when the gas pressure is high, the power of the antenna power supply 121 is high, the power of the antenna high frequency power supply 123 is high, or the power of the bias power supply 141 is high), the electric field formed by the disk-shaped conductor 111 surrounding the light guide rod 141 may create a strong electric field (hollow electric field) in the hollow space 141C.

This electric field may accelerate the ions in the hollow space portion 141C and ionize the gas, by generating plasma in the hollow space 141C. The electric field intensity is greatest at the center of the hollow space portion, so that by inserting an insulating member component 146 in this area, it becomes possible to suppress acceleration of ions and ionization, and to prevent the generation of plasma. Further, the life of the insulating member component 146 can be extended if no through holes for receiving light are formed immediately below the insulating member component 146, so as to prevent ions from passing through the through holes 115B for receiving light formed to the plate 115 toward the insulating member component 146. Thus, the life of the light guide rod 141 can be extended effectively by inserting an insulating member component 146 and preventing abnormal plasma generation.

What is claimed is:

1. A plasma processing apparatus comprising an upper electrode for supplying material gas into a vacuum reactor via a shower plate, a lower electrode opposed to the upper electrode on which is placed a sample being processed, and a detector for detecting light from a surface of the sample being processed via the shower plate, so as to process the sample by generating plasma between the shower plate and the lower electrode; wherein the detector comprises a light transmitting unit including a light guide into which the light is entered and a spectroscope for analyzing the light obtained through the light transmitting unit;

the shower plate includes a plurality of gas through holes through which the material gas passes, and a light introducing through hole through which the light from the sample being processed passes;

the upper electrode has a multilayered structure including a gas transmitting member having passages for the material gas communicated with the gas through holes of the shower plate, and a discharging member connected to a high frequency power supply;

the light transmitting unit is disposed on the discharging member;

the light guide is composed of a first light guide and a second light guide;

the first light guide and the second light guide are cylindrical rods with steps and having multiple varying diameters;

the first light guide is positioned between the second light guide and the spectroscope; and the second light guide has a cylindrical hollow space formed by hollowing an interior of the cylindrical rod of the second light guide, and having a projected structure formed of an electrically insulating member arranged at a center of the cylindrical hollow space thereof so that no light introducing through holes of the shower plate are arranged opposite to the projected structure and a minute gap is formed between the projected structure and the shower plate; and the second light guide has an end portion which faces the shower plate and which extends outwardly to form a flange portion.

2. The plasma processing apparatus according to claim 1, wherein a pipe-shaped member is arranged in the interior of the cylindrical hollow space of the second light guide.

* * * * *